(12) United States Patent
Bressloff et al.

(10) Patent No.: US 9,707,109 B2
(45) Date of Patent: Jul. 18, 2017

(54) STENT WITH ALTERNATING AMPLITUDES

(71) Applicant: Arterius Limited, Leeds, West Yorkshire (GB)

(72) Inventors: Neil W. Bressloff, Highfield (GB); Sanjay Pant, Paris (FR); Kadem Gayad Al-Lamee, Leeds (GB)

(73) Assignee: Arterius Limited, Leeds (GB)

( * ) Notice: Subject to any disclaimer, the term of this patent is extended or adjusted under 35 U.S.C. 154(b) by 0 days.

(21) Appl. No.: 14/994,674

(22) Filed: Jan. 13, 2016

(65) Prior Publication Data

US 2016/0120668 A1    May 5, 2016

Related U.S. Application Data

(63) Continuation of application No. 14/112,884, filed as application No. PCT/GB2012/050882 on Apr. 20, 2015, now Pat. No. 9,271,852.

(30) Foreign Application Priority Data

Apr. 20, 2011    (GB) .................................. 1106757.6

(51) Int. Cl.
*A61F 2/915*    (2013.01)
*A61F 2/86*    (2013.01)

(52) U.S. Cl.
CPC ................ *A61F 2/86* (2013.01); *A61F 2/915* (2013.01); *A61F 2002/91508* (2013.01);
(Continued)

(58) Field of Classification Search
CPC ............. A61F 2002/91508; A61F 2002/91525
(Continued)

(56) References Cited

U.S. PATENT DOCUMENTS 5,938,697 A    8/1999  Killion et al.
6,059,822 A    5/2000  Kanesaka et al.
(Continued)

FOREIGN PATENT DOCUMENTS

JP    2005-348813 A    12/2005
WO    WO 01/64133 A1    9/2001

*Primary Examiner* — Katrina Stransky
*Assistant Examiner* — Wade P Schutte
(74) *Attorney, Agent, or Firm* — Blank Rome LLP

(57) ABSTRACT

A tubular stent has first and second ends and a longitudinal axis therebetween. The tubular stent is formed from a network of struts which defines a cylindrical surface about the longitudinal axis, the struts delineating a plurality of cells within the network, there being rows of cells parallel to the longitudinal axis. At least one cell in each row is a nodal cell. There is an increase in the maximum length parallel to the longitudinal axis of cells from the nodal cell to a first distal cell in the row that is closer to the first or second end of the tubular stent. There is a second distal cell in the row which has a different maximum length parallel to the longitudinal axis from the nodal cell and the first distal cell. The network of struts comprises a plurality of circumferential rings. Each ring extends perpendicularly to the longitudinal axis and the rings are located adjacent to each other parallel to the longitudinal axis to define the cylindrical surface. The circumferential rings are of a wave form. Each circumferential ring has an amplitude parallel to the longitudinal axis, such that each wave form comprises a plurality of peaks which extend towards the axial center of the tubular stent and a plurality of troughs which extend away from the axial center of the tubular stent.

14 Claims, 10 Drawing Sheets

(52) U.S. Cl.
CPC ............... *A61F 2002/91525* (2013.01); *A61F 2002/91541* (2013.01); *A61F 2002/91558* (2013.01); *A61F 2230/0054* (2013.01); *A61F 2250/0067* (2013.01); *F04C 2270/041* (2013.01)

(58) Field of Classification Search
USPC ........................................................ 623/1.15
See application file for complete search history.

(56) References Cited

U.S. PATENT DOCUMENTS

| | | |
|---|---|---|
| 2003/0045926 A1 | 3/2003 | Pinchasik |
| 2004/0024444 A1 | 2/2004 | Moore |
| 2004/0044400 A1 | 3/2004 | Cheng et al. |
| 2004/0073290 A1* | 4/2004 | Chouinard ................ A61F 2/91 |
| | | 623/1.15 |
| 2004/0102837 A1 | 5/2004 | Boyle et al. |
| 2004/0243216 A1 | 12/2004 | Gregorich |
| 2007/0043418 A1 | 2/2007 | Lee et al. |
| 2007/0208411 A1* | 9/2007 | Meyer ..................... A61F 2/856 |
| | | 623/1.15 |
| 2011/0022156 A1 | 1/2011 | Richter et al. |

\* cited by examiner

STENT WITH ALTERNATING AMPLITUDES

FIELD OF THE INVENTION

The present invention relates to a stent and, in particular, a stent of tubular construction that is of a type that may be implanted within a vessel or passage of a patient.

BACKGROUND OF THE INVENTION

There are many medical situations where it is necessary or desirable to implant a stent within a patient in order to prevent or counteract a constriction in a naturally occurring vessel or passage. In this context, a "stent" is an artificial tubular structure which is able to apply force radially outwardly on a vessel or passage of a patient in order to maintain patency of the vessel or passage and permit fluid flow through the vessel or passage.

The most common procedure in which a stent is implanted in a patient is implantation in a coronary artery which has become partially blocked or occluded (referred to as being "stenosed") by a lesion or plaque. In this procedure, a stenosed coronary artery is opened through an angioplasty procedure in which a crimped stent is introduced into the stenosed artery and the stent is expanded within the artery, for example, by using a balloon on a catheter. Expansion of the stent compresses the lesion or plaque blocking the coronary artery and allows blood to flow through the artery without constriction. As part of the procedure, the stent is left in place in the artery, in expanded form, in order to maintain the patency of the artery. In some procedures, prior to implantation of the stent, a pre-dilation step is carried out by expanding a balloon on a catheter within the section of the coronary artery affected by the lesion in order to compress the lesion or plaque prior to insertion of the stent. Vascular stents are also used in other blood vessels aside from coronary arteries and the implantation procedure is similar.

One of the main requirements of a vascular stent is that it can be enlarged from a crimped configuration which has a sufficiently small radial diameter in order to be guided in an angioplasty procedure, to an expanded configuration in which the exterior surface of the stent contacts and engages with the inner surface of the blood vessel. Moreover, in the expanded configuration, the stent must have sufficient radial strength in order to maintain the lumen of the blood vessel open. There are various different forms of construction of vascular stents but a common form is a metal mesh stent in which the stent comprises a network of struts which delineate a plurality of cells within the network. The struts are hinged or otherwise deformable with respect to each other which permits expansion of the stent after implantation. However, more recently, mesh stents have been made from other materials such as biodegradable polymers.

One problem with mesh stents is that of "arterial recoil". After a mesh stent has been expanded, the stent may not have sufficient radial strength to withstand the radially inward force of the blood vessel such that the stent is squeezed and the blood vessel constricts. There are various solutions to this problem, although none is ideal. For example, one solution is to reduce the cell size of the mesh which directly increases the radial strength of the stent. However, the problem with this approach is that decreasing the cell size reduces the flexibility of the stent which can make implantation of the stent difficult because blood vessels are not perfectly cylindrical in shape and thus the natural conformation of a blood vessel may be lost when the stent is implanted.

Another solution is to increase the thickness of the strut size. However, there is evidence that suggests that the thicker the struts of a mesh stent, the greater the likelihood of restenosis after implantation of the stent.

The problem of arterial recoil in mesh stents can occur with metal mesh stents but is particularly a problem with polymer mesh stents which have less intrinsic strength than metal mesh stents.

U.S. Pat. No. 6,059,822 reports on a mesh stent that has large mesh portions at either end of the stent and a small mesh portion at the longitudinal centre of the stent. The small mesh portion has a mesh of a smaller size than the larger mesh portion and is used at the longitudinal centre of the stent where the main lesion is located once the stent is implanted. The small mesh portion provides more radial strength and lessens any chance of prolapse. The ends of the stents, however, have a larger mesh size so as to reduce the damage to healthy tissue parts of the artery in which the stent is located. Thus there are only two different cell sizes in the stent.

However, there is always a demand to improve upon the configuration of mesh stents so as to avoid the problem of arterial recoil along the longitudinal length of the stent whilst maintaining flexibility and minimising arterial injury.

The background to the invention has been explained above in relation to vascular stents but it is to be understood that the present invention is not limited thereto. Stents other than vascular stents exist such as ureteral, urethral, duodenal, colonic and biliary stents, and analogous problems arise with these stents as have been described above in relation to vascular stents.

The present invention seeks to alleviate one or more of the above problems.

SUMMARY OF THE INVENTION

According to one aspect of the present invention there is provided a tubular stent having first and second ends and a longitudinal axis therebetween, the tubular stent being formed from a network of struts which defines a cylindrical surface about the longitudinal axis, the struts delineating a plurality of cells within the network, there being rows of cells extending from the first end to the second end, at least one cell in each row being a central cell, the maximum length parallel to the longitudinal axis of each successive cell from the at least one central cell to the first and second ends of the tubular stent increasing progressively and wherein the network of struts comprises a plurality of circumferential rings, each ring extending perpendicularly to the longitudinal axis and the rings being located adjacent to each other parallel to the longitudinal axis to define the cylindrical surface, the circumferential rings being of a wave form, each circumferential ring having an amplitude parallel to the longitudinal axis, such that each wave form comprises a plurality of peaks which extend towards the axial centre of the tubular stent and a plurality of troughs which extend away from the axial centre of the tubular stent.

It is preferred that the rows of cells are parallel to the longitudinal axis of the tubular stent.

It is preferred that the struts are rigid struts.

Conveniently, the stent is crimpable.

Preferably, the progressive increase in maximum length parallel to the longitudinal axis of successive cells from the axial centre to the first and second ends of the tubular stent comprises a component with a geometric increase.

Advantageously, the circumferential rings comprise central circumferential rings and distal circumferential rings, wherein the central circumferential rings define the at least one central cell of the tubular stent, adjacent central circumferential rings being aligned so that the respective peaks and/or troughs of the central circumferential rings are aligned with each other and linked to each other, the central circumferential rings thus defining the at least one central cell of each row of cells.

Conveniently, the central circumferential rings and the distal circumferential rings are aligned such that where a first distal circumferential ring is adjacent to a second distal circumferential ring or a central circumferential ring, at least some of the peaks of the wave form of the first distal circumferential ring are aligned with at least some of the troughs of the wave form of the second distal circumferential ring or the central circumferential ring and are linked to each other such that adjacent circumferential rings define cells within the network.

Preferably, each distal circumferential ring has a wave form that alternates between a maximum amplitude peak and trough and a minimum amplitude peak and trough.

Advantageously adjacent distal circumferential rings are linked to each other only by the maximum amplitude peaks and troughs.

Conveniently, the peak-peak amplitude of the minimum amplitude peaks and troughs of the distal circumferential rings increases progressively from each distal circumferential ring adjacent to a central circumferential ring to the distal circumferential rings adjacent to one of the ends of the tubular stent.

Preferably, the peak-peak amplitude of the minimum amplitude peaks and troughs of the distal circumferential rings increases geometrically from each distal circumferential ring adjacent to a central circumferential ring to the distal circumferential rings adjacent to one of the ends of the tubular stent.

Advantageously, the peak-peak amplitude of the maximum amplitude peaks and troughs of the distal circumferential rings increases progressively from each distal circumferential ring adjacent to a central circumferential ring to the distal circumferential rings adjacent to one of the ends of the tubular stent.

Conveniently, the peak-peak amplitude of the maximum amplitude peaks and troughs of the distal circumferential rings increases geometrically from each distal circumferential ring adjacent to a central circumferential ring to the distal circumferential rings adjacent to one of the ends of the tubular stent.

Preferably, the at least one central cell is a closed cell.

Conveniently, the central cell can be referred to as the nodal cell as the central cell does not have to be located at the axial centre of the tubular stent.

Advantageously, at least one row of cells comprises at least three cells, preferably at least five cells.

Conveniently, the maximum length parallel to the longitudinal axis of each successive cell from the at least one central cell to the first end increases progressively at the same to, or a different rate from, that at which the maximum length parallel to the longitudinal axis of each successive cell increases progressively from the at least one central cell to the second end.

Preferably, the at least one central cell is the cell or cells closest to the axial centre of the tubular stent. Alternatively, the at least one central cell is not a cell closest to the axial centre of the tubular stent. Instead the, or each, central cell is located closer to the first or second ends of the tubular stent.

According to another aspect of the present invention there is provided a tubular stent having first and second ends and a longitudinal axis therebetween, the tubular stent being formed from a network of struts which defines a cylindrical surface about the longitudinal axis, the struts delineating a plurality of cells within the network, there being rows of cells extending from the first end to the second end, at least one cell in each row being a nodal cell, there being an increase in the maximum length parallel to the longitudinal axis of cells from the at least one nodal cell to a first distal cell that is closer to the first or second end of the tubular stent and wherein the network of struts comprises a plurality of circumferential rings, each ring extending perpendicularly to the longitudinal axis and the rings being located adjacent to each other parallel to the longitudinal axis to define the cylindrical surface, the circumferential rings being of a wave form, each circumferential ring having an amplitude parallel to the longitudinal axis, such that each wave form comprises a plurality of peaks which extend towards the axial centre of the tubular stent and a plurality of troughs which extend away from the axial centre of the tubular stent.

The nodal cell and the first distal cell are in the same row.

Advantageously, there is provided a second distal cell in the row which has a different maximum length parallel to the longitudinal axis from the nodal cell and the first distal cell. Preferably, the maximum length parallel to the longitudinal axis increases from the nodal cell, to the first distal cell and then to the second distal cell in each row.

Conveniently, at least some of the cells are open cells.

Preferably, the stent is crimpable.

Conveniently, the increase in maximum length parallel to the longitudinal axis of cells from the nodal cell of the tubular stent to the first distal cell closer to the first or second end of the tubular stent comprises a component with a geometric increase.

Preferably, the circumferential rings comprise nodal circumferential rings and distal circumferential rings, wherein the nodal circumferential rings define the at least one nodal cell of the tubular stent, adjacent nodal circumferential rings being aligned so that the respective peaks and/or troughs of the nodal circumferential rings are aligned with each other and linked to each other, the nodal circumferential rings thus defining the at least one nodal cell of each row of cells.

Advantageously, the nodal circumferential rings and the distal circumferential rings are aligned such that where a first distal circumferential ring is adjacent to a second distal circumferential ring or a nodal circumferential ring, at least some of the peaks of the wave form of the first distal circumferential ring are aligned with at least some of the troughs of the wave form of the second distal circumferential ring or the nodal circumferential ring and are linked to each other such that adjacent circumferential rings define cells within the network.

Conveniently, each distal circumferential ring has a wave form that alternates between a maximum amplitude peak and trough and a minimum amplitude peak and trough.

Advantageously, the adjacent distal circumferential rings are linked to each other only by the maximum amplitude peaks and troughs.

Preferably, at least some of the adjacent distal circumferential rings are linked to each other by the maximum amplitude peaks and troughs, and by the minimum amplitude peaks and troughs.

Advantageously, there is an increase in the peak-peak amplitude of the minimum amplitude peaks and troughs of the distal circumferential rings from a distal circumferential ring relatively closer to a nodal circumferential ring to a distal circumferential ring relatively further from a nodal circumferential ring.

Conveniently, the peak-peak amplitude of the minimum amplitude peaks and troughs of the distal circumferential rings increases progressively from a distal circumferential ring relatively closer to a nodal circumferential ring to a distal circumferential ring relatively further from the nodal circumferential ring.

Preferably, the peak-peak amplitude of the minimum amplitude peaks and troughs of the distal circumferential rings increases progressively from each distal circumferential ring adjacent to a nodal circumferential ring to the distal circumferential rings adjacent to one of the ends of the tubular stent.

Conveniently, the peak-peak amplitude of the minimum amplitude peaks and troughs increases geometrically.

Advantageously, there is an increase in the peak-peak amplitude of the maximum amplitude peaks and troughs of the distal circumferential rings from a distal circumferential ring relatively closer to a nodal circumferential ring to a distal circumferential ring relatively further from the nodal circumferential ring.

Preferably, the peak-peak amplitude of the maximum amplitude peaks and troughs of the distal circumferential rings increases progressively from a distal circumferential ring relatively closer to a nodal circumferential ring to a distal circumferential ring relatively further from the nodal circumferential ring.

Conveniently, the peak-peak amplitude of the maximum amplitude peaks and troughs of the distal circumferential rings increases progressively from each distal circumferential ring adjacent to a nodal circumferential ring to the distal circumferential rings adjacent to one of the ends of the tubular stent.

Advantageously, the peak-peak amplitude of the maximum amplitude peaks and troughs increases geometrically.

Preferably, the at least one nodal cell is a closed cell.

Advantageously, at least one row of cells comprises at least three cells.

Conveniently, the maximum length parallel to the longitudinal axis of cells from the at least one nodal cell to a distal cell relatively closer to the first end of the tubular stent increases at a different rate from that at which the maximum length parallel to the longitudinal axis of cells increases from the at least one nodal cell to a distal cell relatively closer to the second end of the tubular stent.

Preferably, there is a second nodal cell closer to one of the ends of the tubular stent than the first nodal cell, wherein there is a distal cell between the first and second nodal cells, and wherein the maximum length parallel to the longitudinal axis of cells increases from each nodal cell to the distal cell between the nodal cells.

Conveniently, there is a third nodal cell between the first and second nodal cells, a first intermediate distal cell between the first and the third nodal cells and a second intermediate distal cell between the second and the third nodal cells, wherein the maximum length parallel to the longitudinal axis of cells increases from each of the first and third nodal cells to the first intermediate distal cell and from each of the second and third nodal cells to the second intermediate distal cell.

Advantageously, the at least one nodal cell is the cell or cells closest to the axial centre of the tubular stent.

Preferably, the at least one nodal cell may be located anywhere along the length of the stent. When there is more than one nodal cell, these may or may not be adjacent to each other.

Advantageously, a pharmaceutically active agent is releasably associated with the tubular stent.

In this specification, the terms "longitudinal" and "axial" have the same meaning and are used interchangeably.

In this specification, the term "wave form" means a component, in particular a circumferential ring, whose shape oscillates along its length. The oscillation is in a direction defined as the amplitude of the wave. The oscillation may be a smooth curve such as a sine wave or may be triangle wave form.

DETAILED DESCRIPTION OF THE INVENTION

Figure 1:
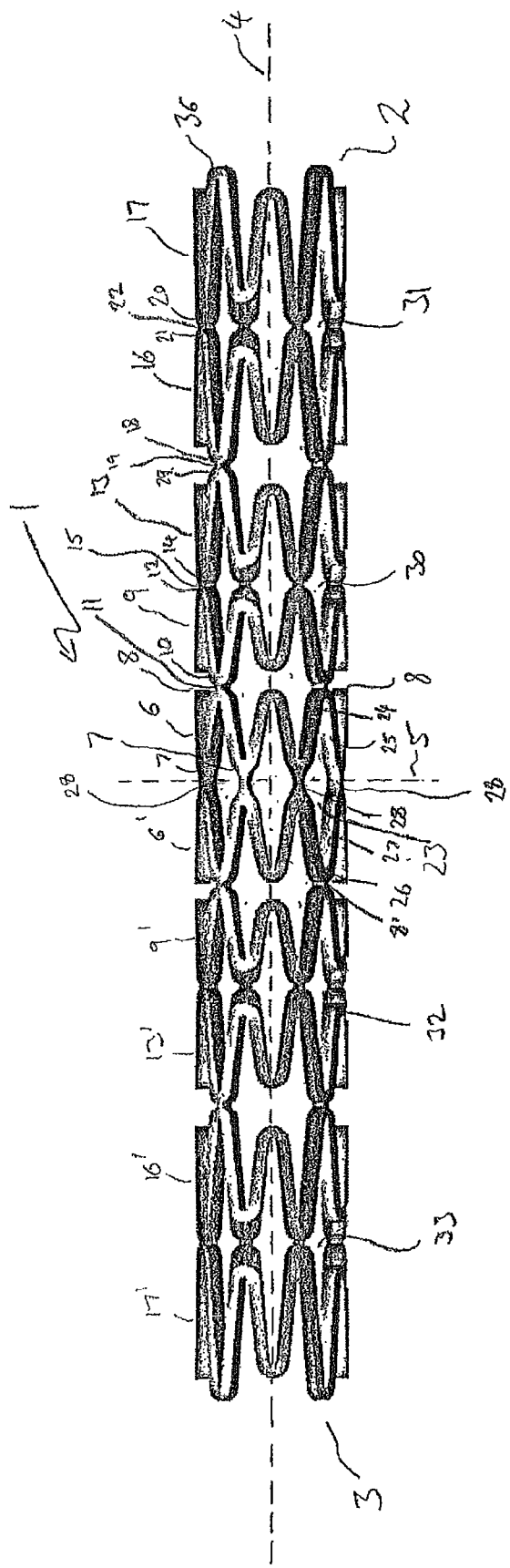
FIG. 1 is a side view of a tubular stent in accordance with one embodiment of the present invention, viewed perpendicular to the longitudinal axis of the stent, with the stent in a pre-crimped configuration.

Referring to FIG. 1, a tubular stent 1 is shown which comprises a first end 2 and a second end 3 and a longitudinal axis 4 therebetween. Equidistant between the first and second ends 2, 3 there is a longitudinal centre 5 of the stent 1 which is a plane perpendicular to the longitudinal axis 4. Adjacent to the longitudinal centre 5 of the stent 1, towards the first end 2 of the stent 1 is a first central ring 6 which extends circumferentially about the longitudinal axis 4 in a wave form having its amplitude parallel to the longitudinal axis 4 of the tubular stent 1. The wave form of the first central ring 6 comprises eight peaks 7 which are each proximal to the longitudinal centre 5 and eight troughs 8 which are each distal from the longitudinal centre 5.

Adjacent to the troughs 8 of the first central ring is provided a second ring 9 which also extends circumferentially about the longitudinal axis 4 and is of wave form, having its amplitude parallel to the longitudinal axis 4 of the tubular stent 1. The wave form of the second ring 9 comprises eight peaks 10 which are each proximal to the longitudinal centre 5 and eight troughs 12 which are each distal from the longitudinal centre 5. The wave form of the second ring 9 will be described in further detail, below. At the present time it need merely be noted that the amplitude of the wave form alternates between a maximum amplitude and a minimum amplitude around the second ring 9. Furthermore, the maximum amplitude of the second ring 9 is greater than the amplitude of the first central ring 6. In addition, the peaks 10 of maximum amplitude of the second ring 9 are aligned with alternate troughs 8 of the first central ring 6 and are connected by a short link 11 which is parallel to the longitudinal axis 4.

Adjacent to the troughs 12 of the second ring 9 is located a third ring 13 which also extends circumferentially about the longitudinal axis 4 and defines a wave form. The wave form of the third ring 13 is similar to the wave form of the second ring 9 in that the amplitude of successive wavelengths alternate between a maximum amplitude and a minimum amplitude. The wave form of the third ring 13 comprises eight peaks 14 which are each proximal to the longitudinal centre 5 and eight troughs 29 which are each distal from the longitudinal centre 5. In addition, the peak-peak maximum amplitude of the wave form of the third ring 13 is greater than the peak-peak maximum amplitude of the wave form of the second ring 9. Furthermore, the peaks with maximum amplitude 14 of the third ring 13 are aligned with the troughs 12 of maximum amplitude of the second ring 9 and are connected by a short link 15 which is parallel to the longitudinal axis 4.

Adjacent to the troughs 29 of the third ring 13 is a fourth ring 16 and, in turn, a fifth ring 17. The fourth and fifth rings 16 and 17 repeat the pattern of the second and third rings 9, 13. More specifically, each of the fourth and fifth rings 16, 17 extends circumferentially about the longitudinal axis 14 and is of a wave form with the amplitude of successive wavelengths alternating between a maximum amplitude and a minimum amplitude. The wave form of the fourth ring 16 comprises eight peaks 18 which are each proximal to the longitudinal centre 5 and eight troughs 21 which are each distal from the longitudinal centre 5. The wave form of the fifth ring 17 comprises eight peaks 20 which are each proximal to the longitudinal centre 5 and eight troughs 36 which are each distal from the longitudinal centre 5. The maximum peak-peak amplitude is successively greater from the second ring 9 to the third ring 13 to the fourth ring 16 to the fifth ring 17. Moreover, the fourth and fifth rings 16, 17 are aligned with respect to each other and with respect to the third ring 13 such that the peaks 18 of maximum amplitude of the fourth ring 16 are adjacent to the troughs 29 of maximum amplitude of the third ring 13 and are connected by a link 19 and, likewise, the peaks 20 of maximum amplitude of the fifth ring 17 are aligned with the troughs 21 of maximum amplitude of the fourth ring 16 and are connected by a short link 22 that is parallel to the longitudinal axis 4.

The structure of the stent 1 has been described from the longitudinal centre 5 to the first end 2. However, the stent 1 from the longitudinal centre 5 to the second end 3 is a mirror image through the plane of the longitudinal centre 5 with second central ring 6' and second, third, fourth and fifth rings 9', 13' 16', 17', mirroring the first central ring 6 and the second, third, fourth, fifth rings 9, 13, 16, 17, respectively. At the longitudinal centre 5, the peaks 7, 7' of the first and second central rings 6, 6' are aligned and are linked to each other by links 28 that are parallel to the longitudinal axis of the tubular stent 1.

It is to be appreciated therefore, that the circumferential rings 6, 6', 9, 9', 13, 13', 16, 16', 17, 17' together define a cylindrical surface about the longitudinal axis 4. It is also to be noted that the circumferential rings fall into two categories: the central rings 6, 6' and the other rings 9, 9', 13, 13', 16, 16', 17, 17' which will be referred to herein as distal rings. The central rings 6, 6' are linked to each other at each peak 7, 7' of their respective waveforms by links 28. However, the distal rings adjacent to the central rings (i.e. the second rings 9, 9') are linked to the central rings only via alternate peaks 10, 10', namely the peaks of maximum amplitude. Similarly the other distal rings (i.e. the third to fifth rings 13, 13', 16, 16', 17, 17') are only linked to the adjacent distal ring closer to the axial centre 5 via alternate peaks, namely the peaks of maximum amplitude. In this respect, the tubular stent 1 has an open cell design since not all aligned peaks and troughs between adjacent distal rings are joined.

In conjunction with the links 11, 15, 19, 22, the first to fifth rings 6, 6', 9, 9', 13, 13', 16', 16', 17, 17' together form a network of struts which delineate a plurality of cells within the network. For instance, a central cell 23 is defined by first and second struts 24, 25 which correspond to a section of the first central ring 6 between a peak 7 and a trough 8 and the trough 8 and a second peak 7 respectively. Likewise the third and fourth struts 26, 27 correspond to a section between a first peak 7' of the second central ring 6' which is aligned with the first peak 7 of the first central ring 7 to a trough 8' of the second central ring 6' and the section of the second central ring 6' from the trough 8' to a second peak 7' of the second central ring 6' which is aligned with the second peak 7 of the first central ring 6. The central cell 23 is also defined by first and second links 28 which are parallel to the longitudinal axis 4 and which connect the first peak 7, 7' of the first and second central rings, 6, 6' and the second peaks 7, 7' of the first and second central rings 6, 6'. Thus, together, the first to fourth struts 24, 25, 26, 27 and the first and second links, 28 define the first exemplary cell.

A cell 30 in position "1" (i.e. adjacent to and in the same row as the central cell 23) is defined by the struts which correspond to a section of the second ring 9 between two consecutive maximum amplitude troughs 12 and a section of the third ring 13 between two consecutive maximum amplitude peaks 14 and the respective links 15 that join the troughs 12 of the second ring 9 with the peaks 14 of the third ring 13.

A cell 31 in position "2" (i.e. adjacent to and in the same row as the cell 30 in position two but further from the central cell 23) is defined by the struts which correspond to a section of the fourth ring 16 between two consecutive maximum amplitude troughs 21 and a section of the fifth ring 17 between two consecutive maximum amplitude peaks 20 and the respective links 22 that join the troughs 21 of the fourth ring 16 with the peaks 20 of the fifth ring 17.

A cell 32 in position "−1" is also present and is the mirror image of the cell 30 in position "1" about the longitudinal centre.

A cell 33 in position "−2" is also present and is the mirror image of the cell 31 in position "2" about the longitudinal centre.

The length of each cell in the row increases progressively (i.e. adjacent cells do not have the same length) from the central cell 23 to the cell at position "1" which is closer to the first end 2 and then to the cell at position "2" which is closest to the first end 2. Likewise, the length of each cell in the row increases progressively from the central cell 23 to the cell at position "−1" which is closer to the second end 3 and then to the cell at position "−2" which is closest to the second end 3.

Figure 2:
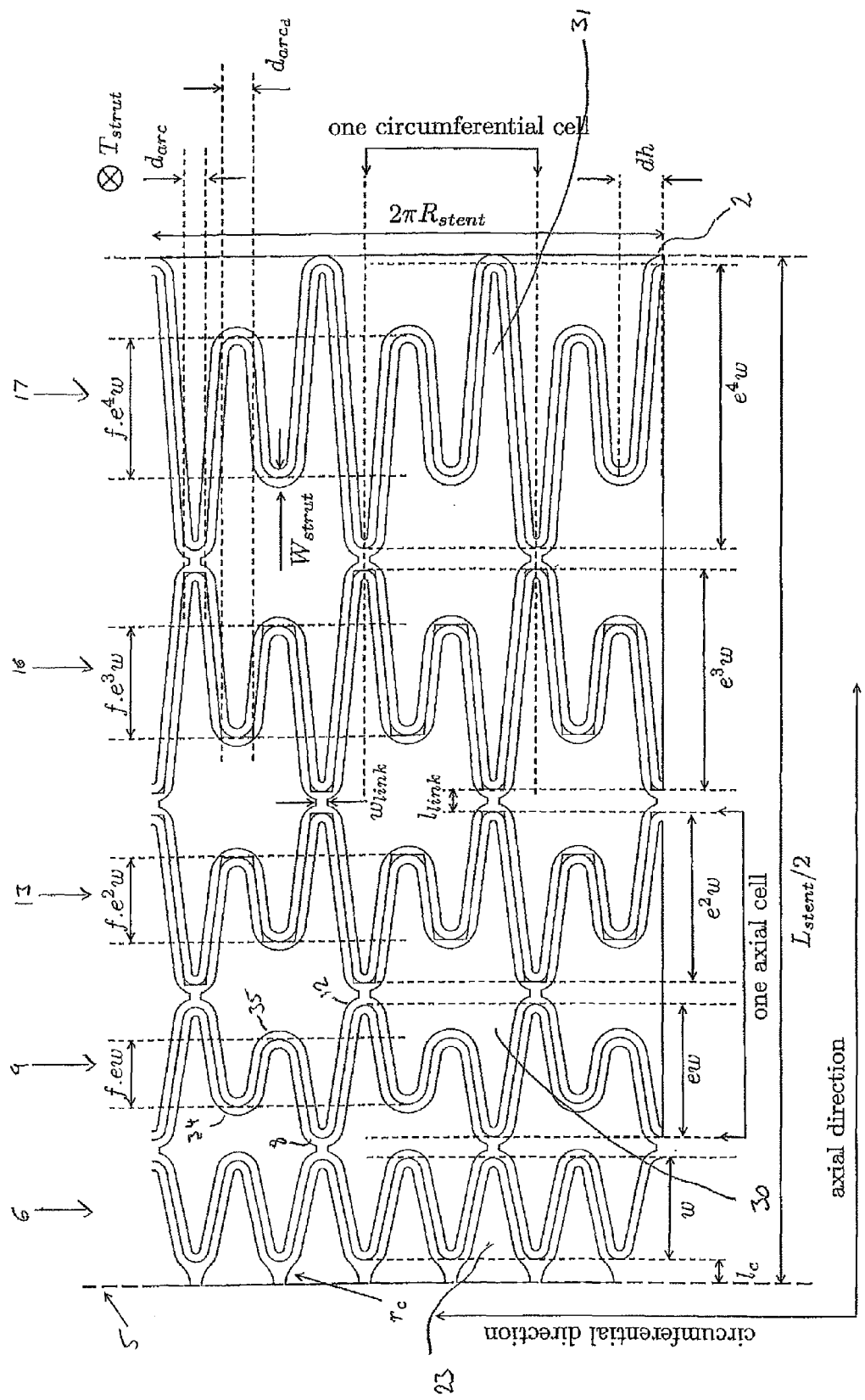
FIG. 2 is a plan view of a flattened out section of a stent in accordance with the embodiment shown in FIG. 1.
Figure 5:
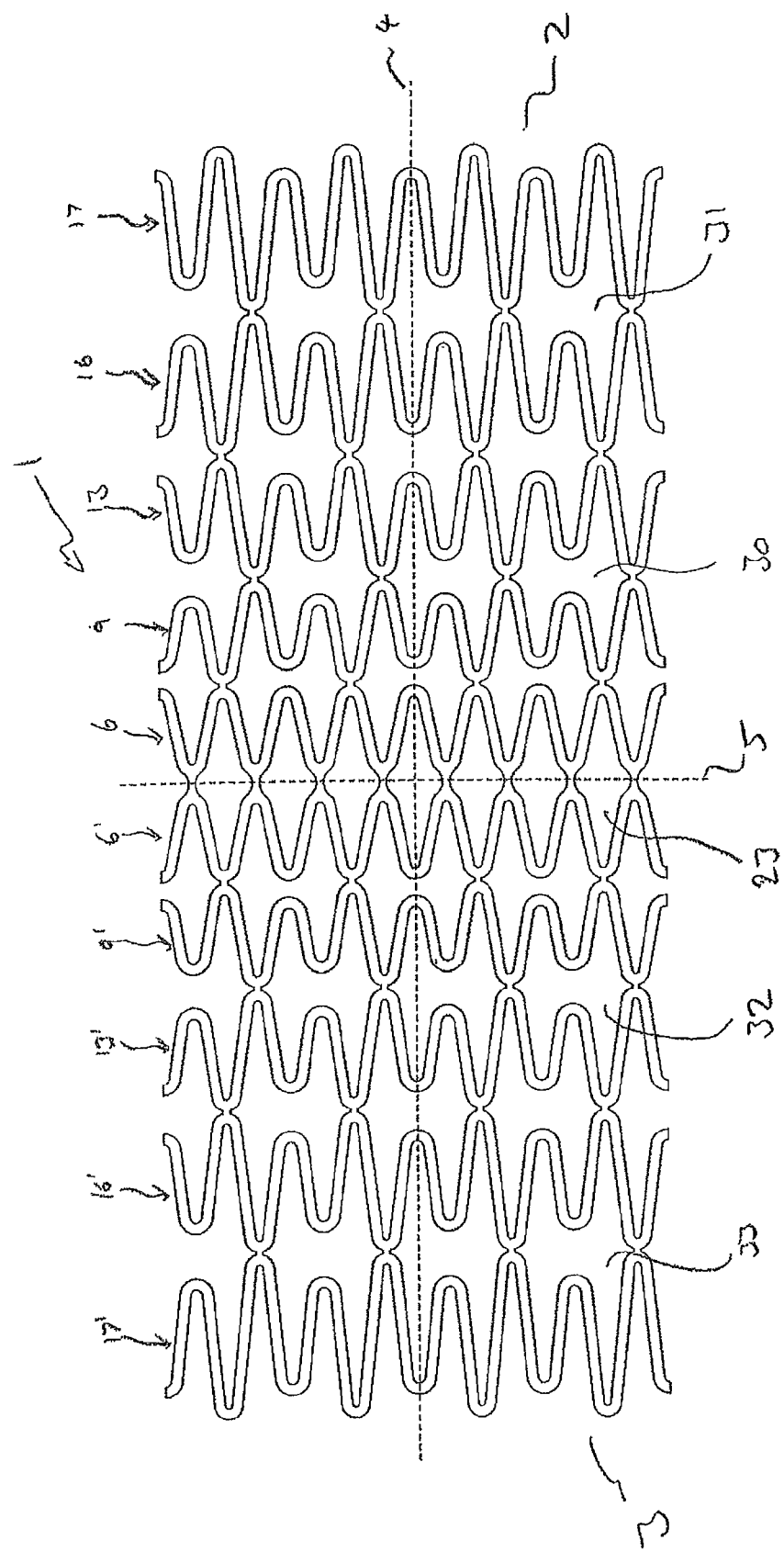
FIG. 5 is a plan view of the entire tubular stent of the embodiment shown in FIG. 1, flattened out.

Referring to FIG. 2 a section of the stent 1 is shown, flattened out to illustrate more clearly the repeating structure of the stent and the mathematical relationship between the various elements of the stent. It is to be appreciated that FIG. 2 shows only a section of the complete stent shown in FIG. 1. The complete stent of FIG. 1 is shown flattened out in FIG. 5.

Shown on FIG. 2 are the parameters that govern the design of this embodiment of the tubular stent 1. The following parameters are independent— a) $T_{strut}$—Strut thickness in radial direction (thickness of the extruded tube)
b) $W_{strut}$—Strut width in the circumferential direction.
c) $l_c$—half length of the central link 28 between respective peaks 7, 7' of the first and second central rings 6, 6'.
d) $l_{link}$—length of the links 11, 12, 19, 22 between respective maximum amplitude peaks and maximum amplitude troughs of adjacent rings.
e) $w_{link}$—circumferential width of the links 11, 12, 19, 22 (similar to $W_{strut}$).
f) NoX—Number of cells in the axial direction (i.e. parallel to the longitudinal axis 4).
g) NoY—Number of cells in the circumferential direction.
h) $L_{stent}$—Total length of the stent 1.
i) Rstent—Pre crimping inner radius of the stent 1 (inner radius of the extruded tube).
j) $d_{arc}$—Diameter of the arc/semi-circle at the link locations.
k) w—distance parallel to the longitudinal axis 4 between peaks 7 and troughs 8 of the first central ring 6.
l) f—The factor by which the minimum amplitude in each ring 9, 13, 16, 17 (except the first central ring 6) are smaller than their respective maximum amplitude.
m) $r_c$—radius of the arc in the central links 28 in the cells defined by the first and second central rings 6, 6'.

The following parameters have to be derived— a) dh—quarter length of each cell in the circumferential direction.
b) e—The ratio between the lengths (i.e. the distance in the direction parallel to the longitudinal axis from maximum amplitude peaks to maximum amplitude troughs) of consecutive rings.
c) $d_{arc_d}$—Derived diameter of the arcs/semi-circles in each ring at the non-link locations.

The parameter dh is calculated according to equation [1]—

$$dh = \frac{2\pi R_{stent}}{4 NoY} \quad [1]$$

The parameter 'e' is calculated by first considering the equality of equation [2] in the axial direction:

$$l_c + (NoX - 1)l_{link} + w + \sum_{i=1}^{NoX-1} e^i w = \frac{L_{stent} - W_{strut}}{2} \quad [2]$$

The last two terms in the left hand side of equation [2] can we written as equation [3]

$$w + \sum_{i=1}^{NoX-1} e^i w = \frac{w(e^{NoX} - 1)}{(e-1)}; e > 1 \quad [3]$$

Substituting equation [3] in equation (2) gives equation [4]

$$l_c + (NoX - 1)l_{link} + \frac{w(e^{NoX} - 1)}{(e-1)} = \frac{L_{stent} - W_{strut}}{2} \quad [4]$$

This is an implicit equation in 'e' as e cannot be explicitly expressed in terms of other parameters. Newton's iterative method is used to solve this equation. Let f(e) be defined as equation [5]

$$f(e) = l_c + (NoX - 1)l_{link} + \frac{w(e^{NoX} - 1)}{(e-1)} - \frac{L_{stent} - W_{strut}}{2} \quad [5]$$

The solution of f(e)=0 gives the appropriate value of e. The method is started by guessing a value for e, say e=1.1, to initiate the Newton's method. Note that the derivative of f(e) can be calculated analytically. To calculate the new value of e, the formula of equation [6] is used $$e_{new} = e_{prev} - \frac{f(e)}{f'(e)} \quad [6]$$

This process is repeated until the difference between $e_{new}$ and $e_{prev}$ is less than $10^{-6}$, thereby yielding the value of e that satisfies the equality constraint in the axial direction.

Next the value of $d_{arc_d}$ is calculated. If the axial length of the $i^{th}$ ring (i=0, 1, 2, 3, and 4 for the central, first, second, third and fourth rings 6/6', 9/9', 13/13', 16/16', and 17/17', respectively) is $w_i$, then $d_{arc_d}$ for that ring, is given by equation [7]

$$d_{arc_d} = \frac{2(dh(w_i - f \cdot w_i) + 0.5 d_{arc}(f \cdot w_i + xx))}{w_i + xx} \quad [7]$$

$$\text{where } xx = \frac{w_i d_{arc}}{2(dh - d_{arc})}$$

Geometrical Constraints

The following geometrical constraints, set forth in equations [8], [9] and [10], arise while using the above described embodiment of the tubular stent 1.

$$l_c \geq W_{strut} \quad [8]$$

$$l_{link} \geq W_{strut} \quad [9]$$

$$dh > W_{strut} \quad [10]$$

Determination of Numerical Bounds on w

In order to determine the numerical bounds on w equation [2] is considered. Rearranging equation [2] yields the following:

$$w + \sum_{i=1}^{NoX-1} e^i w = \frac{L_{stent} - W_{strut}}{2} - l_c - (NoX - 1)l_{link} \quad [11]$$

$$\Rightarrow w = \frac{\frac{L_{stent} - W_{strut}}{2} - l_c - (NoX - 1)l_{link}}{\left(1 + \sum_{i=1}^{NoX-1} e^i\right)}$$

e>1 is desired since this provides increasing cell length from the longitudinal centre 5 of the tubular stent 1 to the respective first and second ends 2, 3. For the limiting case of e=1, the inequality of equation [12] can be obtained $$w \leq \frac{\frac{L_{stent} - W_{strut}}{2} - l_c - (NoX - 1)l_{link}}{NoX} \quad [12]$$

This relation of equation [12] gives the upper bound on w.

Figure 4:
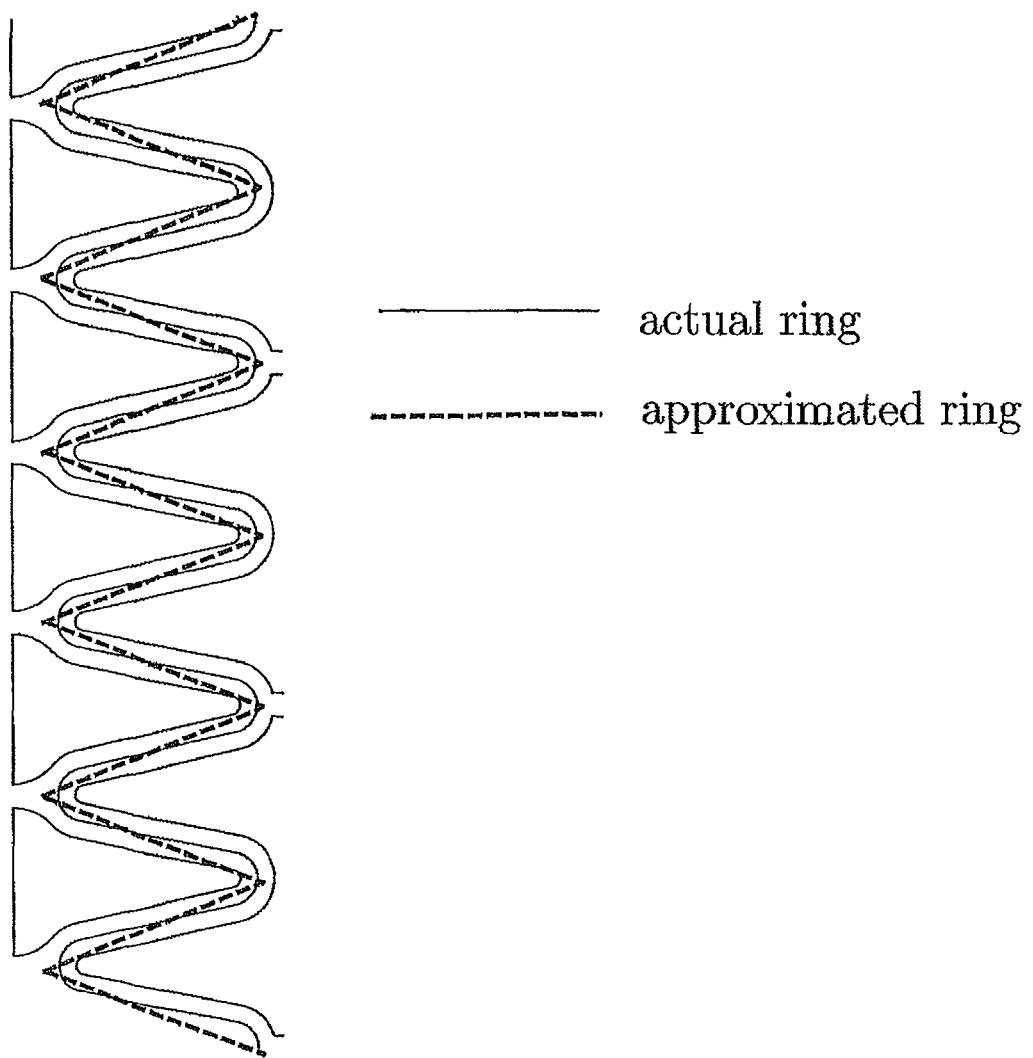
FIG. 4 is a schematic view of one portion of a tubular stent in accordance with the embodiment shown in FIG. 1.

The lower bound on w is governed by the geometrical constraint that the length of the central ring in the circumferential plane should be greater than the circumference of the final stent diameter desired after expansion. Let $R_f$ be the final expansion diameter. Although, an exact expression for the length of the central ring is possible, it yields a mathematically unwieldy equation and so the following simplification is made to simplify the expression. In particular, the central ring is approximated with linear segments without the semi-circular joints. Using this approximation, illustrated in FIG. 4, the length of the central ring in the circumferential plane can be written as equation [13]

$$l_{ring} = 4NoY\sqrt{dh^2 + w^2} \quad [13]$$

Geometrical constraint, as discussed above, dictates the requirements of equation [14]

$$l_{ring} \geq n_{safe} 2\pi R_f; \; n_{safe} \geq 1 \quad [14]$$

where $n_{safe}$ is a safety factor to be specified.

Using equations [13], [14], and [1], the relation of equation [15] can be shown $$w \geq \frac{\pi}{2NoY}\sqrt{(n_{safe}R_f)^2 - R_{stent}^2} \quad [15]$$

This relation of equation [15] gives the lower bound on w.

The maximum value of w constrains the NoX values. In particular, for a given $L_{stent}$ the maximum value of w limits the NoX values for which e>1 can be obtained. Using equation [12] one can deduce the formula of equation [16]

$$NoX = \text{floor}\left[\frac{\frac{L_{stent} - W_{strut}}{2} - l_c + l_{link}}{l_{link} + w_{max}}\right] \quad [16]$$

Determination of Numerical Bounds on $d_{arc}$

The lower bound in $d_{arc}$ is zero. For the upper bound, the inequality of equation [17] can be deduced from FIG. 2

$$d_{arc_d} \leq dh \quad [17]$$

Equation [17] can be used with equation [7] to deduce the upper bound in $d_{arc}$.

Determination of Numerical Bounds on $W_{strut}$

Theoretically, the lower and upper bounds for $W_{strut}$ are zero and dh respectively.

The first central ring 6 and the second to fifth rings 9, 13, 16, 17 are shown in FIG. 2. As can be seen, the first central ring 6 is of repeating wave form configuration with a peak-peak amplitude of w.

The second ring 9 is of a wave form where the wave form alternates between a maximum peak-to-peak amplitude of ew between a peak of maximum amplitude 8 and a trough of maximum amplitude 12 and a minimum peak-to-peak amplitude of f.ew between a minimum amplitude peak 34 and a minimum amplitude trough 35.

The third to fifth rings 13, 16, 17 have similar wave forms which alternate between maximum and minimum amplitudes and whose maximum and minimum amplitudes progressively increase from ring to ring from the longitudinal centre 5 of the stent 1 to the first end 2. The relative dimensions of the maximum peak-peak amplitude and the minimum peak-peak amplitude of each ring is summarized in Table 1.

TABLE 1

| Ring | Maximum Peak-Peak Amplitude | Minimum Peak-Peak Amplitude |
|---|---|---|
| Central | w | w |
| Second | ew | f. ew |
| Third | $e^2 w$ | f. $e^2 w$ |
| Fourth | $e^3 w$ | f. $e^3 w$ |
| Fifth | $e^4 w$ | f. $e^4 w$ |

It is also to be noted that each cell extends in the axial direction (i.e. parallel to the longitudinal axis 4) from a maximum amplitude peak of one ring (or a peak of the central ring) to the maximum amplitude trough of the adjacent ring in the axial direction. Furthermore, each cell extends in the circumferential direction from the link connecting a maximum amplitude trough of the one ring (or a trough of the central ring) and the abutting maximum amplitude peak of the adjacent ring to the adjacent link in the circumferential direction connecting a maximum amplitude trough of the one ring (or a trough of the central ring) and the abutting maximum amplitude peak of the adjacent ring.

It is also to be understood that that the maximum length of the cells in the axial direction (i.e. the distance from the maximum amplitude peak of one ring (or a peak of the central ring) to the maximum amplitude trough of the adjacent ring in the axial direction) are based on the centre construction lines (see FIG. 2) and are as shown in Table 2.

TABLE 2

| Cell Position | Item in FIGS. 1 and 2 | Maximum Length |
|---|---|---|
| −2 | 33 | $e^3 w + e^4 w + l_{link}$ |
| −1 | 32 | $ew + e^2 w + l_{link}$ |
| central | 23 | $2(w + l_c)$ |
| 1 | 30 | $ew + e^2 w + l_{link}$ |
| 2 | 31 | $e^3 w + e^4 w + l_{link}$ |

Thus the maximum length of each cell comprises a variable component based on the value of e, if it is assumed that the other components ($l_c$ or $l_{link}$) are constant.

Furthermore, the variable component increases geometrically from cell to cell from the central cell towards either end of the tubular stent. More specifically, the ratio of the variable component of the adjacent cells is shown in Table 3.

TABLE 3

| Cells | Ratio of Variable Component of Maximum Lengths |
|---|---|
| Cell 1 to Central Cell | $\dfrac{e(1+e)}{2}$ |
| Cell 2 to Cell 1 | $e^2$ |

For a stent suitable for implantation at a focal lesion, a preferred value for e would be in the range 1.08-1.14. For a stent suitable for implantation at a diffused lesion, a preferred value for e would be in the range 1.00-1.08. A value of f in the range 0.80-0.95 is preferred as this balances the strength and flexibility of the stent and other factors such as the performance of the stent in delivering a drug associated with the stent (further details of which are provided below) which militates against large cell sizes.

However, it is to be appreciated that in other embodiments the ratio of maximum axial lengths of adjacent cells may increase according to a different geometric formula or may increase arithmetically, only, and not have a geometric component.

In the above described embodiment, the length of each cell increases progressively from the central cell 23 to the cells at the first and second ends 2, 3 of the tubular stent 1. However, in alternative embodiments, the length of each cell increases progressively by a different rate (e.g. by a different geometric value) from the central cell 23 to the first end 2 than to the second end 3. For example, the value of a may be greater from the central cell 23 to the first end 2 than from the central cell 23 to the second end 3. In alternative embodiments, the cell size does not increase progressively from the central cell 23 to the first and second ends 2, 3, but increases only part of the way from the central cell 23 to the first and second ends 2, 3. In further embodiments, the cell size does not increase from central cell 23 to the cells at the first and second ends 2, 3, but, instead, there may be any combination of increase and decrease in cell size from central cell 23 to the first and second ends 2, 3. Such embodiments are particularly suitable for implantation in blood vessels which have multiple lesions in which the stent is such that the regions of small cell size are the same distance apart as the lesions and thus, on implantation, the stent is positioned to align the regions of small cell size with the respective lesions. An example of such a stent will be described in further detail below.

In the above described embodiment, the tubular stent 1 comprises five cells 33, 32, 23, 30, 31 arranged consecutively, parallel to the longitudinal axis 4 of the tubular stent 1. However, in other embodiments, the tubular stent 1 comprises more than five cells. In these alternative embodiments, each row of the tubular stent 1 has a central cell 23 as described in the embodiment shown in FIG. 1 but additional cells are added at the first and second ends 2, 3 by the addition of the further rings. In other embodiments, the tubular stent 1 comprises fewer than five cells in which case cells are omitted from the first and/or second ends 2, 3 but it is to be appreciated that there is a minimum of three cells in a row. In still further embodiments, more than one central cell is provided. For example, in one embodiment, the tubular stent is provided with four central circumferential rings which define two central cells of equal size and which are located on either side of the longitudinal centre 5 of the stent. Each central cell is of the same length in the direction parallel to the longitudinal axis 4.

In further embodiments of the invention, the or each central cell 23 is not located at or near the longitudinal centre 5 of the tubular stent 1. Instead, the or each central cell 23 is located closer to the first or second ends 2, 3 of the tubular stent and one of the cells at position "1", "2", "−1" or "−2" (or another position if more than five cells are present in each row) is closest to the longitudinal centre 5 of the tubular stent 1. For this reason, the term "nodal cell" is used as a more generic descriptor of a "central cell" in this specification. In these embodiments the progressive increase in cell size from the central cell 23 to the cell at the first end 2 may be the same as or different from the progressive increase in cell size from the central cell 23 to the cell at the second end 3 of the tubular stent 1. Furthermore, there may be the same or a different number of cells (and thus circumferential rings) from the central cell 23 to the cell at the first end 2 than the number of cells from the central cell 23 to the cell at the second end 3.

Figure 3:
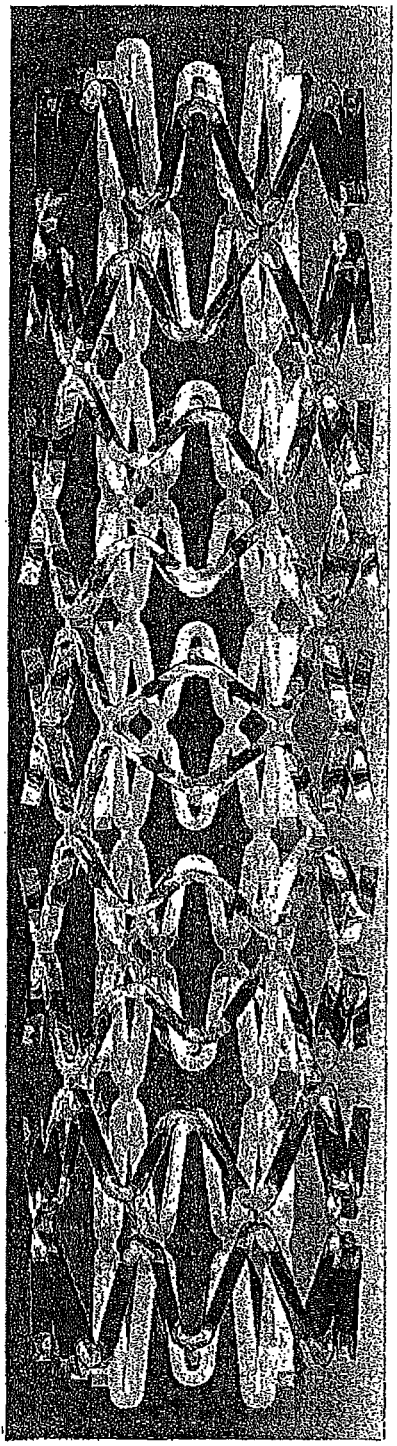
FIG. 3 is a side view of the stent depicted in the embodiment shown in FIG. 1, viewed perpendicular to the longitudinal axis of the stent, with the stent in a pre-crimped configuration and with the stent shown in an expanded configuration superimposed thereon.

In use, a patient is selected for implantation of a stent of the present invention based on criteria such as the presence of a plaque or lesion in a blood vessel such as a coronary artery. The tubular stent 1 is inserted in crimped configuration into a blood vessel such as a coronary artery in an angioplasty procedure as is known in the art. Once the tubular stent is located at the section of blood vessel that is blocked or partially blocked due to the lesion or plaque, the tubular stent is expanded, in situ, for example by inflation of an angioplasty balloon within the tubular stent. Upon expansion, the tubular stent 1 enlarges to an expanded configuration as is shown in FIG. 3. As is shown in FIG. 3, in the expanded configuration, the wave form of the rings 6, 6', 9, 9', 13, 13', 16, 16', 17, 17' becomes straighter thus enlarging each of the cells in the circumferential direction. The overall axial length of the tubular stent 1 is foreshortened but only by a relatively small amount.

In the process of expansion of the tubular stent, the lesion or plaque is compacted and the lumen of the blood vessel is expanded thus reducing or removing any blood flow constriction. The tubular stent is made from a rigid material that is capable of plastic deformation such as a stainless steel alloy or a biodegradable polymer. Thus the tubular stent 1 substantially retains the expanded configuration after the angioplasty balloon is deflated and removed and the surgical procedure is concluded. In practice, the tubular stent 1 is compressed slightly by the radial pressure of the blood vessel after deflation of the balloon but the tubular stent 1 nevertheless remains close to the expanded configuration shown in FIG. 3. Moreover, the plaque or lesion is maintained compacted by the expanded tubular stent after the procedure and the blood vessel patency is likewise maintained by the expanded tubular stent. Thus the tubular stent 1 is of sufficient radial strength to hold open an artery with a lesion. Of particular note is that the central cell of the tubular stent 1 is relatively small and thus has considerable radial strength which resists axial compression by the blood vessel which would otherwise result in blocking, or partial blocking, of the blood vessel. However, while the progressively greater cell size of cells from the central cell to either end 2, 3 of the tubular stent 1 progressively reduces radial strength, it also progressively reduces damage to the vessel wall and progressively increases the axial flexibility of tubular stent 1. This allows the portions of the tubular stent 1 that are further from the plaque or lesion and which are therefore required to have less radial strength to flex and adopt the shape and configuration of the blood vessel in which they are located.

While the above described embodiment relates to a procedure carried out on a blood vessel that is already blocked or partially blocked it is to be understood that in other embodiments the stent is inserted as a precautionary measure, prior to any blocking of the blood vessel.

The above described embodiments are an open cell design of tubular stent. That is to say, aligned peaks and troughs of adjacent distal circumferential rings are not all joined (although the central cell is a closed cell). However, it is to be appreciated that the present invention is not limited to open cell designs and in alternative embodiments a tubular stent may have closed cells other than the central cell. In further embodiments a tubular stent is provided having a closed cell design, that is to say, a stent in which all cells are closed cells.

Figure 6:
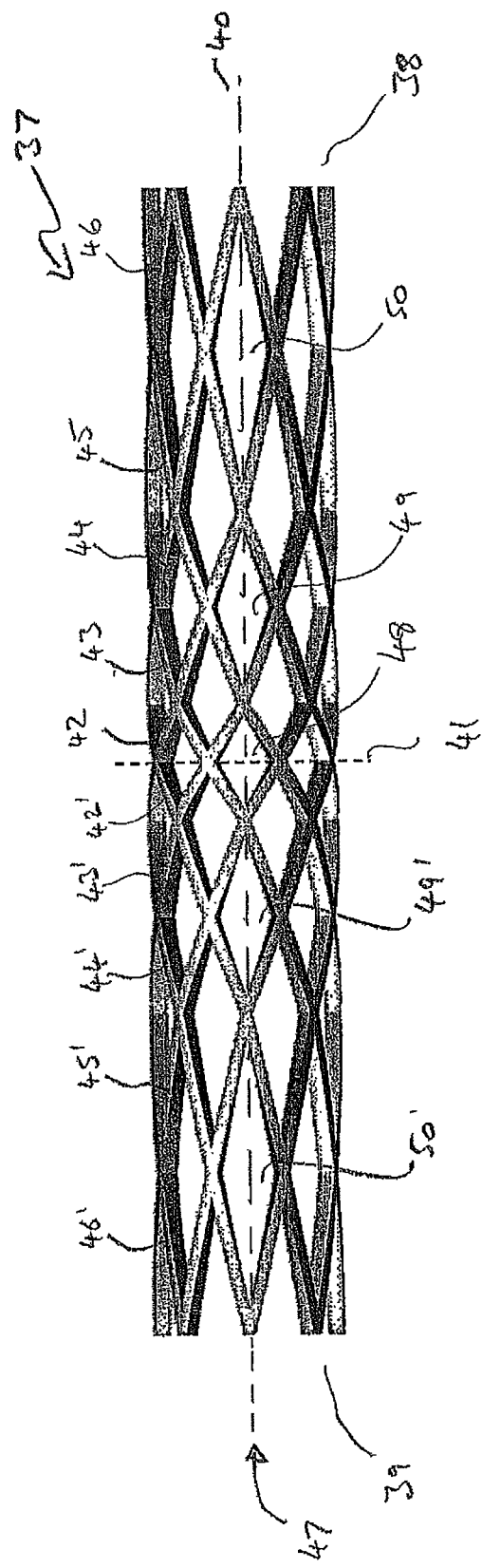
FIG. 6 is a side view of a tubular stent in accordance with another embodiment of the present invention, viewed perpendicular to the longitudinal axis of the stent, with the stent in a pre-crimped configuration.

Referring to FIG. 6, a tubular stent 37 which is of a closed cell design is shown. The tubular stent 37 has first and second ends 38, 39 and a longitudinal axis 40 therebetween. Equidistant between the first and second ends 38, 39 there is a longitudinal centre 41 of the stent 37 which is a plane perpendicular to the longitudinal axis 40. Adjacent to the longitudinal centre 41 is a first central circumferential ring 42 which extends circumferentially about the longitudinal axis 40 in a wave form having its amplitude parallel to the longitudinal axis 40 of the tubular stent 37. Adjacent to the first circumferential ring 42 are first, second, third and fourth distal circumferential rings 43, 44, 45, 46 arranged sequentially and parallel thereto. Each of the distal circumferential rings are also of wave form and also have their amplitudes parallel to the longitudinal axis 40 of the tubular stent 37.

The amplitude of each circumferential ring increases progressively from the first central ring 42 to the first distal circumferential ring 43 and then through each of the other distal circumferential rings 44, 45, 46 to the first end 40. The wave form of each of the first central circumferential ring 42 and the distal circumferential rings 43, 44, 45, 46 comprises eight peaks which are each proximal to the longitudinal centre 41 and eight troughs which are each distal from the longitudinal centre 41. The first central circumferential ring 42 and the distal circumferential rings 43, 44, 45, 46 are aligned with each other so each and every peak of each of the second to fourth distal circumferential rings is aligned with and joined to a trough of its respective adjacent ring closer to the longitudinal centre 41 and each and every peak of the first distal circumferential ring is aligned with and joined to a trough of the first central circumferential ring 42. The peaks and troughs join in an "X" formation without any additional component linking them parallel to the longitudinal axis 40.

The structure of the stent 37 has been described from the longitudinal centre 41 to the first end 38. However, the stent 37 from the longitudinal centre 41 to the second end 39 is a mirror image through the plane of the longitudinal centre 41 with a second central ring 42' and first, second, third, and fourth distal rings 43', 44', 45', 46', mirroring the first central ring 42 and the first, second, third, and fourth distal rings 43, 44, 45, 46, respectively. At the longitudinal centre 41, the peaks of the first and second central rings 42, 42' are aligned and are joined to each other. The peaks join in an "X" formation without any additional component linking them parallel to the longitudinal axis 40.

Thus the central and distal circumferential rings 42, 42', 43, 43', 44, 44', 45, 45', 46, 46' define rows of cells parallel to the longitudinal axis 40 of the tubular stent 37. For example, one row of cells 47 comprises a central cell 48 at the longitudinal centre 41, a cell 49 at position "1" closer to the first end 38 and a cell 50 at position "2" adjacent to the first end 38. Likewise, a cell 49' is at position "−1" adjacent to the central cell but closer to the second end 47 of the tubular stent 37 and a cell 50' is a position "−2" adjacent to the second end 39.

The maximum length of each cell in the direction parallel to the longitudinal axis 40 increases progressively from the central cell 48 to the cell 49 at position "1" and then to the cell 50 at position "2". Similarly the length of each cell increases in the other direction from the central cell 48 to the cell 49' at position "−1" and then to the cell 50' at position "−2". In alternative embodiments, there may be any combination of increase and decrease in the cell size from central cell 48 to first and second ends 38, 39.

In the embodiment shown in FIG. 6, the tubular stent 37 is of closed cell design since aligned peaks and troughs of adjacent distal circumferential rings are all joined. In alternative embodiments, there may be any combination of closed and open cells along the length of the stent.

Figure 7:
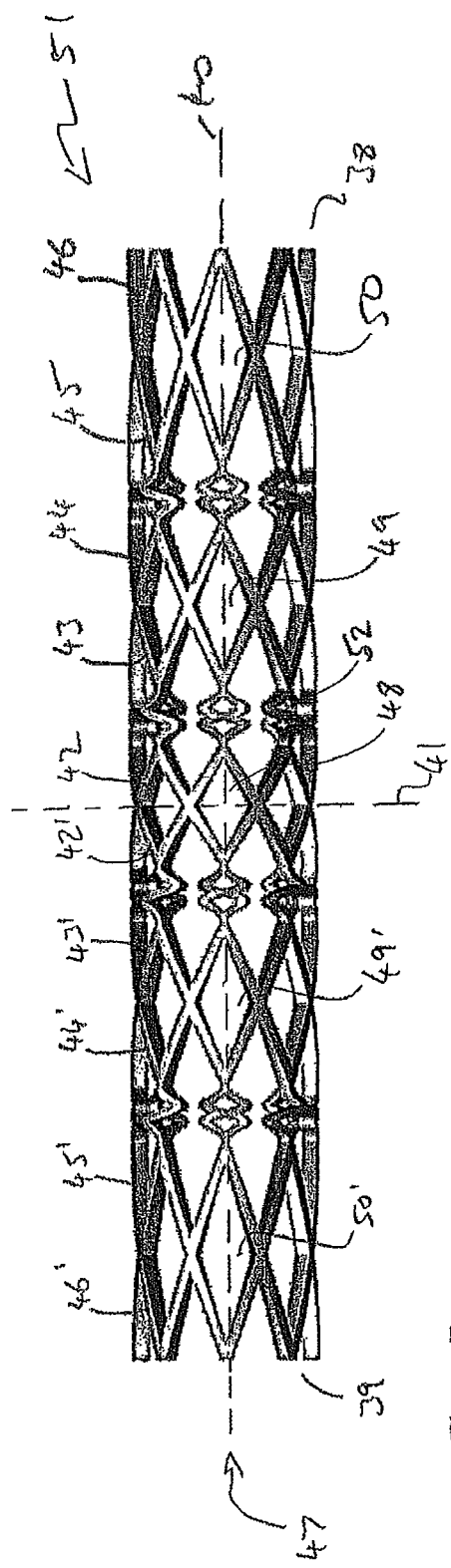
FIG. 7 is a side view of a tubular stent in accordance with a further embodiment of the present invention, viewed perpendicular to the longitudinal axis of the stent, with the stent in a pre-crimped configuration.

Referring to FIG. 7, a tubular stent 51 is shown in accordance with another embodiment of the present invention. The tubular stent 51 of FIG. 7 is similar to the tubular stent 37 shown in FIG. 6 and like components are shown with the same reference numerals. However the tubular stent 51 of FIG. 7 is different from the tubular stent 37 shown in FIG. 6 because at each junction 52 between the first central ring 42 and the first distal ring 43 and between the second distal ring 44 and the third distal ring 45, the respective peaks and troughs are connected by an "S"-shaped linker leading from the first end 38 to the longitudinal centre 41, rather than in an "X" formation. The same applies to the second central ring 42', and the first, second and third distal rings 43', 44', 45' towards the second end 39 of the tubular stent 51. The "S"-shaped linker provides flexibility and limits foreshortening of the tubular stent 51.

Figure 8:
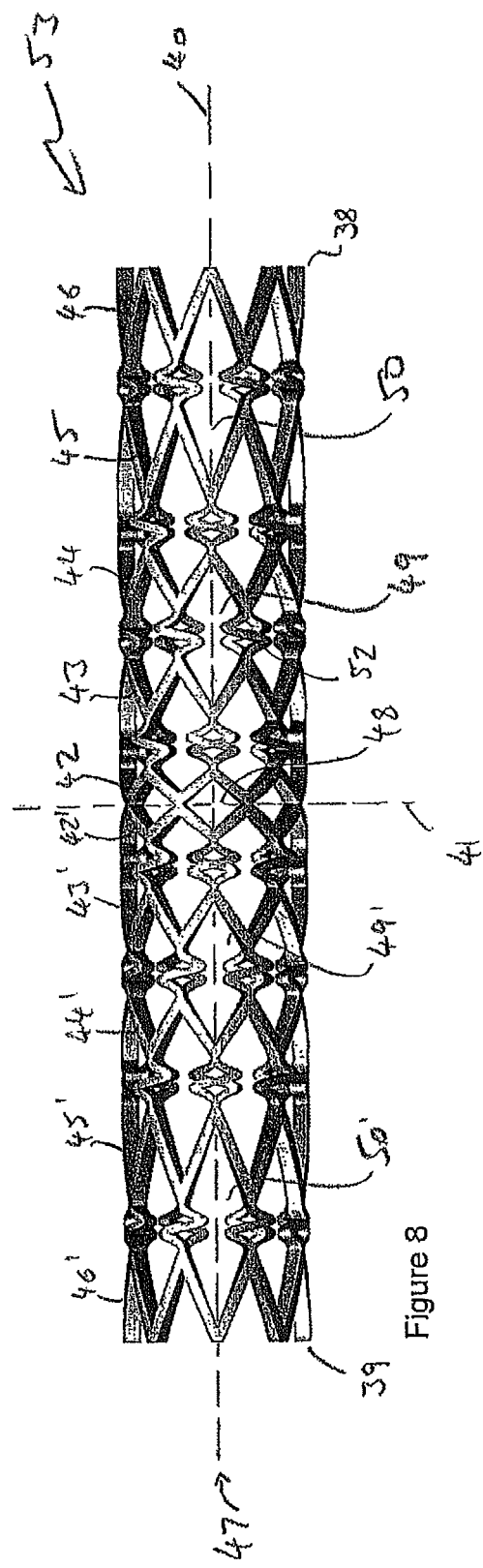
FIG. 8 is a side view of a tubular stent in accordance with another embodiment of the present invention, viewed perpendicular to the longitudinal axis of the stent, with the stent in a pre-crimped configuration.

Referring to FIG. 8, a tubular stent 53 is shown in accordance with another embodiment of the present invention. The tubular stent 53 of FIG. 8 is similar to the tubular stent 51 shown in FIG. 7 and like components are shown with the same reference numerals. However the tubular stent 53 of FIG. 8 is different from the tubular stent 51 shown in FIG. 7 because every junction 52 between peaks and troughs of adjacent distal circumferential rings 43, 43', 44, 44', 45, 45', 46, 46' and at the junctions between the first distal circumferential rings 43, 43' and the first and second central circumferential rings 42, 42' is connected by an "S"-shaped linker leading from the first or second end 38, 39 to the longitudinal centre 41, rather than in an "X" formation. This increases the flexibility of the tubular stent 53.

Figure 9:
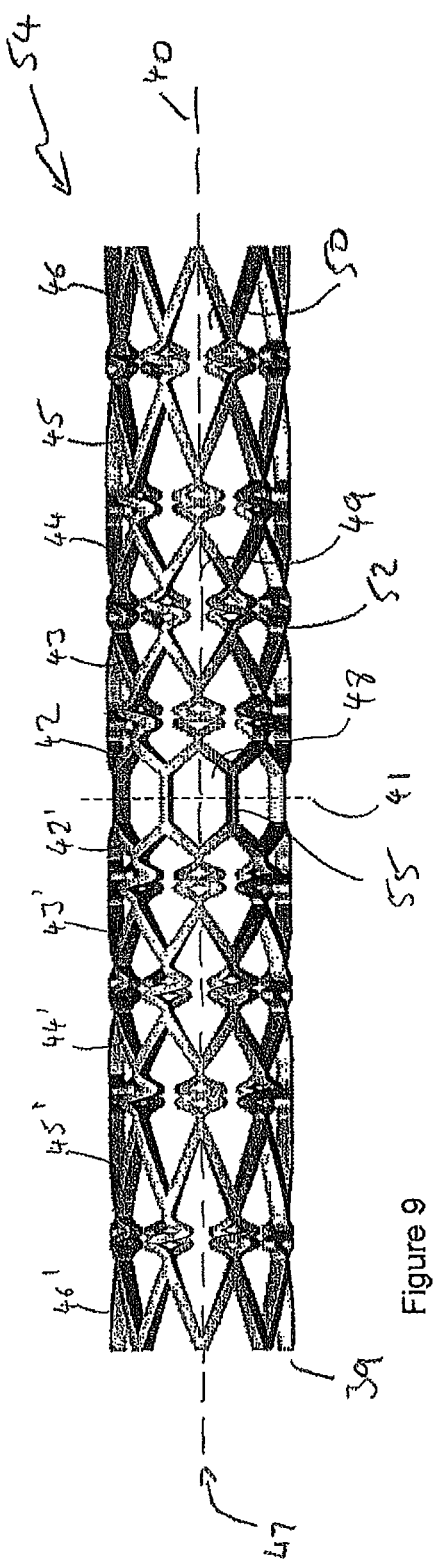
FIG. 9 is a side view of a tubular stent in accordance with yet another embodiment of the present invention, viewed perpendicular to the longitudinal axis of the stent, with the stent in a pre-crimped configuration.

Referring to FIG. 9, a tubular stent 54 is shown in accordance with another embodiment of the present invention. The tubular stent 54 of FIG. 9 is similar to the tubular stent 53 shown in FIG. 8 and like components are shown with the same reference numerals. However the tubular stent 54 of FIG. 9 is different from the tubular stent 53 shown in FIG. 8 because the respective peaks of the first and second central circumferential rings 42, 42' do not meet. Instead, each peak of the first central circumferential ring 42 is joined to the aligned peak of the second central circumferential ring 42' via a bridge 55 that runs parallel to the longitudinal axis

40. Thus the central cell 48 is hexagonal. The tubular stent 54 of this embodiment has extended support away form the centre of the stent.

In particular, in some embodiments, there is a plurality of nodal cells, separated along the length of the stent. In such embodiments, the cell size increases, decreases or increases and decreases between nodal cells. Such embodiments result in patient and/or disease-specific stents. Such stents can be used to treat complex, eccentric or diffuse and/or focal diseases within the blood vessels. An example of such a stent is shown in FIG. 10.

Figure 10:
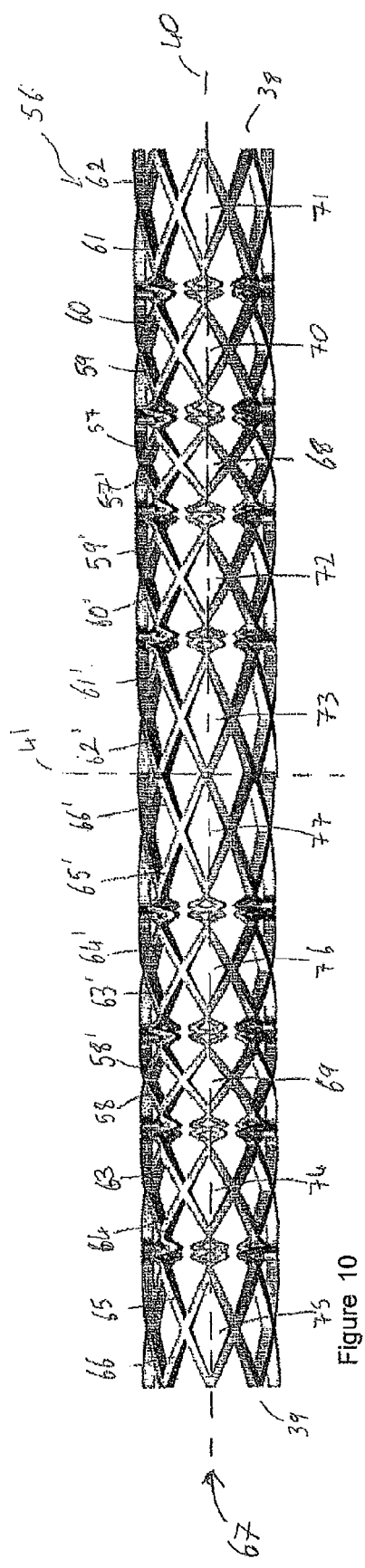
FIG. 10 is a side view of a tubular stent in accordance with a further embodiment of the present invention, viewed perpendicular to the longitudinal axis of the stent, with the stent in a pre-crimped configuration.

Referring to FIG. 10, a tubular stent 56 is shown in accordance with another embodiment of the present invention. The tubular stent 56 has first and second ends 38, 39 and a longitudinal axis 40 therebetween. Equidistant between the first and the second ends 38, 39 there is a longitudinal centre 41 of the stent 56 which is a plane perpendicular to the longitudinal axis 40. Between the longitudinal centre 41 and the first end 38 is a first nodal circumferential ring 57 which extends circumferentially around the longitudinal axis 40 in a wave form having its amplitude parallel to the longitudinal axis 40 of the tubular stent 56. Adjacent to the first nodal circumferential ring 57, distal to the longitudinal centre 41, are first, second, third and fourth distal circumferential rings 59, 60, 61, 62 arranged sequentially and parallel thereto. Each of the distal circumferential rings is also of wave form and also has its amplitude parallel to the longitudinal axis 40 of the tubular stent 56.

The amplitude of each circumferential ring increases from the first nodal circumferential ring 57 to the first distal circumferential ring 59 and then through to each of the other distal circumferential rings 60, 61, 62 to the first end 38. The wave form of each of the first nodal circumferential rings 57 and the distal circumferential rings 59, 60, 61, 62 comprises eight peaks which are each proximal to the longitudinal centre 41 and eight troughs which are each distal from the longitudinal centre 41. The first nodal circumferential ring 57 and the distal circumferential rings 59, 60, 61, 62 are aligned with each other so each and every peak of the second to fourth distal circumferential rings is aligned with and joined to a trough of its respective adjacent ring closer to the longitudinal centre 41 and each and every peak of the first distal circumferential ring is aligned with and joined to a trough of the first nodal circumferential ring 57. At each junction between the first nodal circumferential ring 57 and the first distal ring 59 and between the second distal ring 60 and the third distal ring 61, the respective peaks and troughs are connected by an "S"-shaped linker leading from the first end 38 to the longitudinal centre 41. At each junction between the first distal ring 59 and the second distal ring 60 and between the third distal ring 61 and the fourth distal ring 62, the respective peaks and troughs are joined in an "X" formation without any additional component linking them parallel to the longitudinal axis 41.

Adjacent to the first nodal circumferential ring 57, relatively proximal to the longitudinal centre 41, is a second nodal circumferential ring 57' and counterpart first, second, third and fourth distal circumferential rings 59', 60', 61' and 62' mirroring the first nodal circumferential ring 57 and first, second, third and fourth distal circumferential rings 59, 60, 61, 62, respectively. The peaks of the first and second nodal circumferential rings 57, 57' are aligned and are joined to each other. The peaks join in an "X" formation without any additional component linking them parallel to the longitudinal axis 40.

The structure of the stent 56 has been defined from the longitudinal centre 41 to the first end 38. However, the stent 56 from the longitudinal centre to the second end is the mirror image through the plane of the longitudinal axis 41 with third and fourth nodal circumferential rings 58, 58' and fifth, sixth, seventh and eighth distal circumferential rings and their counterparts 63, 63', 64, 64', 65, 65', 66, 66' mirroring the first and second nodal circumferential rings 57, 57' and the first, second, third and fourth distal circumferential rings and their counterparts 59, 59', 60, 60', 61, 61', 62, 62' respectively. At the longitudinal centre 41, the peaks of the fourth and eighth counterpart distal circumferential rings 62', 66' are aligned and joined to each other. The peaks join in an "X" formation without any additional component linking them parallel to the longitudinal axis 40.

Thus, the nodal and distal circumferential rings 57, 57', 58, 58', 59, 59', 60, 60', 61, 61', 62, 62', 63, 63', 64, 64', 65, 65', 66, 66' define rows of cells parallel to the longitudinal axis 40 of the tubular stent 56. For example, one row of cells 67 comprises a first nodal cell 68, defined by the first and second nodal circumferential rings 57, 57', and a second nodal cell 69, defined by third and fourth nodal circumferential rings 58, 58'. Adjacent to the first nodal cell 68 is a first distal cell 70 relatively closer to the first end 38, and a second distal cell 71 adjacent to first end 38. Adjacent to the first nodal cell 68 is a third distal cell 72 relatively further from the first end 38 and a fourth distal cell 73 adjacent to the longitudinal centre 41. Adjacent to the second nodal cell 69 is a fifth distal cell 74 relatively closer to the second end 39 and a sixth distal cell 75 adjacent to the second end 39. Adjacent to the second nodal cell 69 and relatively further from the second end 39 is a seventh distal cell 76, and an eighth distal cell 77 adjacent to the longitudinal centre 41.

The maximum length of each cell in the direction parallel to the longitudinal axis 40 increases from the first nodal cell 68 to the first distal cell 70 and then to the second distal cell 71. Similarly the length of each cell increases in the other direction from the first nodal cell 68 to the third distal cell 72 and then to the fourth distal cell 73. As the tubular stent 56 is a mirror image through the plane of the longitudinal centre 41, the maximum cell length parallel to the longitudinal axis 40 increases from the second nodal cell 69 to the fifth distal cell 74 and then to the sixth distal cell 75. Similarly the length of each cell increases in the other direction from the second nodal cell 69 to the seventh distal cell 76 and then to the eighth distal cell 77. Thus, working from the first nodal cell 68 to the second nodal cell 69, the maximum cell length increases to the longitudinal centre 41 and then decreases to the second nodal cell 69.

In use of this embodiment, the stent 56 is implanted into a blood vessel as described in the previous embodiments. However, the stent 56 of this embodiment is specifically adapted for implantation in blood vessels at sites where there are two lesions. The stent 56 is such that the first nodal cell 68 and the second nodal cell 69 are the same distance apart as the centres of the two lesions. On implantation, the stent 56 is located in the blood vessel so that the first and second nodal cells 68, 69 are aligned with each lesion, respectively. Thus the stent 56 has greatest radial strength at the locations corresponding to the positions of the two lesions and there is gradually increasing flexibility of the stent along the sections away from and between the first and second nodal cells 68, 69.

It is to be understood that in further embodiments of the present invention, stents are provided with more than two nodal cells. In these embodiments, the stents are adapted for implantation in blood vessels having more than two lesions.

In the above described embodiments, drugs or other pharmaceutically active agents may be releasably associated with the tubular stent 1, the drugs being released after implantation of the stent 1 into a blood vessel. Typically, the drugs are anti-inflammatory or anti-proliferative or anti-thrombotic drugs which control the inflammation response or restenosis or thrombosis of the blood vessel upon implantation of the stent 1.

The invention claimed is:

1. A tubular stent having first and second ends and a longitudinal axis therebetween, the tubular stent being formed from a network of struts which defines a cylindrical surface about the longitudinal axis, the struts delineating a plurality of cells within the network, there being rows of cells parallel to the longitudinal axis, at least one cell in each row being a nodal cell, there being an increase in the maximum length parallel to the longitudinal axis of cells from the at least one nodal cell to a first distal cell in the row that is closer to the first or second end of the tubular stent and there being a second distal cell in the row which has a different maximum length parallel to the longitudinal axis from the nodal cell and the first distal cell and wherein the network of struts comprises a plurality of circumferential rings, each ring extending perpendicularly to the longitudinal axis and the rings being located adjacent to each other parallel to the longitudinal axis to define the cylindrical surface, the circumferential rings being of a wave form, each circumferential ring having an amplitude parallel to the longitudinal axis, such that each wave form comprises a plurality of peaks which extend towards the axial center of the tubular stent and a plurality of troughs which extend away from the axial center of the tubular stent, wherein:

the circumferential rings comprise nodal circumferential rings and distal circumferential rings, wherein the nodal circumferential rings define the at least one nodal cell of the tubular stent, adjacent nodal circumferential rings being aligned so that the respective peaks and/or troughs of the nodal circumferential rings are aligned with each other and linked to each other, the nodal circumferential rings thus defining the at least one nodal cell of each row of cells;

the nodal circumferential rings and the distal circumferential rings are aligned such that where a first distal circumferential ring is adjacent to a second distal circumferential ring or a nodal circumferential ring, at least some of the peaks of the wave form of the first distal circumferential ring are aligned with at least some of the troughs of the wave form of the second distal circumferential ring or the nodal circumferential ring and are linked to each other such that adjacent circumferential rings define cells within the network; and each distal circumferential ring has a wave form that alternates between a maximum amplitude peak and trough and a minimum amplitude peak and trough, wherein the peak-peak amplitude of the maximum amplitude peaks and troughs of the distal circumferential rings increases progressively from a distal circumferential ring relatively closer to a nodal circumferential ring to a distal circumferential ring relatively further from the nodal circumferential ring, and wherein the peak-peak amplitude of the maximum amplitude peaks and troughs increases geometrically.

2. A tubular stent according to claim 1, wherein the stent is crimpable.

3. A tubular stent according to claim 1, wherein the increase in maximum length parallel to the longitudinal axis of cells from the nodal cell of the tubular stent to the first distal cell comprises a component with a geometric increase.

4. A tubular stent according to claim 1, wherein adjacent distal circumferential rings are linked to each other only by the maximum amplitude peaks and troughs.

5. A tubular stent according to claim 1, wherein at least some of the adjacent distal circumferential rings are linked to each other by the maximum amplitude peaks and troughs, and by the minimum amplitude peaks and troughs.

6. A tubular stent according to claim 1, wherein there is an increase in the peak-peak amplitude of the minimum amplitude peaks and troughs of the distal circumferential rings from a distal circumferential ring relatively closer to a nodal circumferential ring to a distal circumferential ring relatively further from a nodal circumferential ring.

7. A tubular stent according to claim 6, wherein the peak-peak amplitude of the minimum amplitude peaks and troughs of the distal circumferential rings increases progressively from a distal circumferential ring relatively closer to a nodal circumferential ring to a distal circumferential ring relatively further from the nodal circumferential ring.

8. A tubular stent according to claim 6, wherein the peak-peak amplitude of the minimum amplitude peaks and troughs increases geometrically.

9. A tubular stent according to claim 1, wherein the at least one nodal cell is a closed cell.

10. A tubular stent according to claim 1, wherein the maximum length parallel to the longitudinal axis of cells from the at least one nodal cell to a distal cell relatively closer to the first end of the tubular stent increases at a different rate from that at which the maximum length parallel to the longitudinal axis of cells increases from the at least one nodal cell to a distal cell relatively closer to the second end of the tubular stent.

11. A tubular stent according to claim 1, wherein there is a second nodal cell closer to one of the ends of the tubular stent than the first nodal cell, wherein there is a distal cell between the first and second nodal cells, and wherein the maximum length parallel to the longitudinal axis of cells increases from each nodal cell to the distal cell between the nodal cells.

12. A tubular stent according to claim 1, wherein there is a third nodal cell between the first and second nodal cells, wherein there is a first intermediate distal cell between the first and the third nodal cells and a second intermediate distal cell between the second and the third nodal cells, and wherein the maximum length parallel to the longitudinal axis of cells increases from each of the first and third nodal cells to the first intermediate distal cell and from each of the second and third nodal cells to the second intermediate distal cell.

13. A tubular stent according to claim 1, wherein the at least one nodal cell is the cell or cells closest to the axial center of the tubular stent.

14. A tubular stent according to claim 1, wherein a pharmaceutically active agent is releasably associated with the tubular stent.

* * * * *

UNITED STATES PATENT AND TRADEMARK OFFICE
CERTIFICATE OF CORRECTION

PATENT NO.       : 9,707,109 B2
APPLICATION NO.  : 14/994674
DATED            : July 18, 2017
INVENTOR(S)      : Neil W. Bressloff et al.

It is certified that error appears in the above-identified patent and that said Letters Patent is hereby corrected as shown below:

The Related U.S. Application Data should read:

(63) Continuation of application No. 14/112,884, filed as application No. PCT/GB2012/050882 on Apr. 20, 2012, now Pat. No. 9,271,852.

Signed and Sealed this
Seventeenth Day of October, 2017

Joseph Matal
*Performing the Functions and Duties of the
Under Secretary of Commerce for Intellectual Property and
Director of the United States Patent and Trademark Office*